United States Patent [19]

Seki et al.

[11] Patent Number: 5,799,533
[45] Date of Patent: Sep. 1, 1998

[54] DISTRIBUTED PRESSURE SENSOR AND METHOD FOR MANUFACTURING THE SAME

[75] Inventors: Yoshikazu Seki; Makoto Shimojo; Sigeru Sato, all of Tsukuba, Japan

[73] Assignee: Director-General of Agency of Industrial Science and Technology, Tokyo, Japan

[21] Appl. No.: 622,151

[22] Filed: Mar. 27, 1996

[30] Foreign Application Priority Data

May 12, 1995 [JP] Japan .................. 7-114239

[51] Int. Cl.⁶ .................. A61B 5/103; H01C 10/00
[52] U.S. Cl. .................. 73/172; 338/99
[58] Field of Search .................. 73/172, 862.68; 128/779; 338/99, 204, 208, 47, 114; 600/592, 595; 433/68; 324/699, 716

[56] References Cited

U.S. PATENT DOCUMENTS

| | | | |
|---|---|---|---|
| 4,208,648 | 6/1980 | Naumann | 338/99 |
| 4,745,301 | 5/1988 | Michalchik | 307/119 |
| 4,866,412 | 9/1989 | Rzepczynski | 338/114 |
| 5,060,527 | 10/1991 | Burgess | 73/862.68 |

FOREIGN PATENT DOCUMENTS

| | | | |
|---|---|---|---|
| 55-42021 | 3/1980 | Japan . | |
| 62-102127 | 5/1987 | Japan . | |
| 2198237 | 6/1988 | United Kingdom | 73/862.68 |
| 1574 | 3/1987 | WIPO | 73/172 |

*Primary Examiner*—Diego F. F. Gutierrez
*Assistant Examiner*—Willie Morris Worth
*Attorney, Agent, or Firm*—Sterne, Kessler, Goldstein & Fox P.L.L.C.

[57] ABSTRACT

A distributed pressure sensor is constructed such that a wire-like electrode member is arranged in the vertical (row) direction so that electrode surfaces alternately appear on the surface and the rear surface of a sheet-shaped pressure sensitive electrically conductive material, and moreover, a wire-like electrode is arranged also in the lateral (line) direction at right angles to the vertical (row) direction, and intersections defined by the electrode members arranged in the vertical direction and the lateral direction are located such that the pressure sensitive electrically conductive material is sandwiched from both the surfaces. The distributed pressure sensor has high flexibility and exhibits improved durability to repeated bending.

17 Claims, 3 Drawing Sheets

DISTRIBUTED PRESSURE SENSOR AND METHOD FOR MANUFACTURING THE SAME

BACKGROUND OF THE INVENTION

1. Field of the Invention

The present invention relates generally to a distributed pressure sensor employable in the field of a medical care, a welfare service or the like and to a method for manufacturing the same. More particularly, the present invention relates to a distributed pressure sensor which is suitable for use in measuring various pressure distributions, e.g., a body pressure distribution, a sole pressure distribution, a seizing pressure distribution or the like and to a method for manufacturing the same.

2. Description of the Related Art

It has hitherto been known that a distributed pressure sensor is constructed by combining electrodes with a sheet-shaped pressure sensitive electrically conductive material of which electrical resistance value varies depending on pressure. When pressure is exerted on a pressure sensitive electrically conductive material, its volume is reduced. This causes more particles of an electrically conductive material, such as carbon particles or the like, which are distributed substantially uniformly in the pressure sensitive electrically conductive material to contact with each other. As a result, the pressure sensitive electrically conductive material has a decreased electrical resistance value. Variation of the electrical resistance value can be measured based on the electrical resistance value between electrodes disposed at a distance in the order of submillimeters, e.g., 100 to 1,000 μm. Various distributed pressure sensors have been constructed which utilize the pressure sensitive electric electrically conductive material. Examples of conventional pressure sensors include the following.

FIG. 1 is a schematic exploded perspective view which shows an example of the structure of a conventional distributed pressure sensor having a three-layered structure. This pressure sensor includes two electrode sheets 101 and 102 which have each stripe-shaped electrodes 103 and 104 and a pressure sensitive electrically conductive material 105, which is clamped between the stripe-shaped electrodes 103 and 104. The electrodes 103 and 104 extend at right angles to each other. The parts where the stripe-shaped electrodes 103 and 104 intersect at right angles to each other when viewed in an imaginary projected plan view serve as a pressure detecting portion.

FIG. 2 is a schematic exploded perspective view which shows another example of the structure of a conventional distributed pressure sensor having a two-layered structure. As shown in FIG. 2, the distributed pressure sensor includes a flexible base plate 110 and a pressure sensitive electrically conductive material sheet 111 provided on the flexible base plate 110. On the base plate 110 are provided a pair of electrodes. More particularly, a plurality of outer electrodes 112 are provided on an upper surface of the flexible base plate 110 and a plurality of inner electrodes 113 are provided on a lower surface of the plate 110. The outer and inner electrodes 112 and 113 are at a distance in the order of submillimeters. The pressure sensitive electrically conductive material sheet 111 is arranged on pairs of the electrodes 112 and 113. Wiring 114 connected to the outer electrodes 112 is formed on the upper surface of the flexible base plate 110 and wiring 115 connected to the inner electrodes 113 is formed on the lower or rear surface of the flexible base plate 110. Intersections are defined by lines of the wiring 114 connected to the outer electrodes 112 and rows of the wiring 115 connected to the inner electrodes 113 when viewed in an imaginary projected plan view. With this construction, selection of a particular line and a particular row gives a pressure sensing or detecting portion.

As shown in FIG. 3, still another example of a conventional distributed pressure sensor as disclosed in Japanese Patent Application Laying-open NO. 296709/1993 includes first plural cables 120 (H1, H2, ..., Hi, ..., Hn) each having a conductor 122 and a sheath 123 and extending horizontally and second plural cables 121 (V1, V2, ..., Vj, ..., Vm) each having a conductor 124 and a sheath 125 and extending vertically to give a fabric-like appearance. Each of the second cables 121 extends while intersecting all the first cables at right angles, and each of the second cables 121 extends alternately above and below the first cables 120, and the sheath portions 123 and 125 of the first cables 120 and the second cables 121 contact each other. The sheath portions 123 and 125 of the first and second cables 120 and 121 are made of a pressure sensitive electrically conductive material.

In addition, as shown in FIG. 4, a conventional pressure distribution sensor disclosed in Japanese Utility Model Application Publication No. 35787/1984 includes three flexible wiring members 130, each of which has three bands 131, 132, and 133 parallel to each other and connected at one ends thereof to form a common terminal. The bands 131, 132, and 133 of the three flexible wiring members 130 are woven so that the bands 131, 132, and 133 run in three directions equiangularly, i.e., at angles of 120° from adjacent ones to form a sheet-like structure having a plurality of intersecting portions. The bands 131, 132, and 133 have each provided thereon a plurality of conductors 134 extending longitudinally and parallel to each other. To each of the intersecting portions is attached a pressure sensitive sensor 135, and an output from each pressure sensitive sensor is taken out via wiring 136.

However, the conventional distributed pressure sensors described above have problems in respect of flexibility and durability to repeated bending.

Generally, in the fields of medical care, welfare services or the like, there has been an increasing need for a measurement of the state of contact between the body of a human and an article, e.g., in terms of a body pressure distribution, a sole pressure distribution, a seizing power distribution or the like for evaluating pleasantness or comfortableness of products or articles such as chairs, beds or the like, which are contacted by human bodies when in use. In this case, it is necessary that the state of contact should be measured in a state as natural as possible, i.e., the operation of measuring itself should not become a disturbance, and that a sensor or sensors be attached in a limited space. In other words, it has been desired to realize a pressure distribution detecting sensor which is flexible and has a thin wall so that it can be designed as having a relatively large area. Also, in the development of a robot, a keen demand for realizing the above-described type of sensor for use as a sensor for sensing its "skin touch."

Evaluating the conventional sensors from these viewpoints, the sensors have insufficient flexibilities. The reason for this is as follows. When tested for flexibility, the pressure sensitive electric electrically conductive material, which generally includes porous silicone rubber and pressure sensitive electrically conductive particles, such as carbon particles or the like, dispersed in the cavities of the porous silicone rubber, has excellent flexibility. However, the electrode sheet is difficult or impossible to bend since the electrode sheet, i.e., a flexible substrate for forming thereon electrodes, is made of a high molecular material such as polyimide or the like and, hence, it is impossible to deform the electrode sheet with a small radius of curvature compared with the aforementioned pressure sensitive electrically conductive material. Thus, in the case where a distributed pressure sensor having two layers or three layers is constructed by combining both the materials, the resultant sensor does not exhibit sufficient flexibility. For this reason, when measuring a seizing power distribution, a seizing action cannot be performed freely by a user who holds the sensor in his or her palm due to hardness of the flexible base plate of the sensor. For example, when a conventional distributed pressure sensor is fitted to a user's finger to measure seizing power distribution, there arises a problem that the user feels strange with the sensor due to shortage of the flexibility of the sensor or he or she fails to feel exact fitness when seizing an article while measuring. Thus, no exact seizing operation can be performed due to the presence of a practical limit. As a result, it is impossible to measure exact pressure distribution.

The conventional distributed pressure sensors have problems with respect to durability to repeated bending since the sensor has a three- or two-layered structure and, hence, when the distributed pressure sensor is bent, there appears a slight slip between the adjacent layers. Thus, when the sensor is repeatedly bent, there arises distortion in each layer. As a result, the sensor fails to be utilized due to the occurrence of wrinkles or the like deformation. In addition, in the case where a large magnitude of force is exerted on the sensor in the tangential direction, there arises a slip between the adjacent layers, so that the sensor is damaged or broken.

SUMMARY OF THE INVENTION

The present invention has been made in consideration of the aforementioned background.

An object of the present invention is to provide a distributed pressure sensor which has an increased flexibility and an improved durability to repeated bending.

Another object of the present invention is to provide a method for manufacturing a distributed pressure sensor which has an increased flexibility and an improved durability to repeated bending.

According to the first embodiment, the present invention provides a distributed pressure sensor comprising: a substrate comprising an electrically conductive material whose electric resistance varies in response to pressure exerted thereon; a first electrode member provided on the substrate, the first electrode member being linear and appearing reciprocating and alternately on both surfaces of the substrate at a predetermined interval; a second electrode member provided on the substrate, the second electrode member being linear and appearing reciprocating and alternately on both surfaces of the substrate at a predetermined interval at right angles to the first electrode member; the first and second electrode members intersecting each other in an imaginary projected plan view; wherein a portion of the first electrode member and a portion of the second electrode member sandwiching the substrate at each intersection in the imaginary projected plan view between the first and second electrode members to define intersection portions.

Here, the first and second linear electrode members may be sewn to the substrate.

The first and second linear electrode members may each comprise a plurality of electrodes arranged equidistantly in the form of a matrix.

The substrate may be provided with a plurality of cuts.

The at least one of the first and second electrode members may be arranged in the cut.

The at least one of the first and second electrode members may be embedded in the cut.

The pressure sensitive conductive material may comprise carbon particles.

The at least one of the first and second electrode members may comprise braided fine wires.

The at least one of the first and second linear electrode members may comprise copper wire plated with a metal selected from the group consisting of gold and silver.

The distributed pressure sensor may further comprise circuitry connected to the first and second electrode members at each intersection portion for correcting data to avoid deviation.

According to the second embodiment, the present invention provides a method for manufacturing a distributed pressure sensor, comprising the steps of: providing a substrate comprising an electrically conductive material whose electric resistance varies in response to pressure exerted thereon; sewing the substrate with a first linear conductor so that the conductor partly appearing reciprocating and alternately on both surfaces of the substrate at a predetermined interval; and sewing the substrate with a second linear conductor so that the conductor partly appearing reciprocating and alternately on both surfaces of the substrate at a predetermined interval at right angles to the first electrode member.

According to the present invention, the distributed pressure sensor is constructed such that a wire-like electrode member is arranged on a sheet-shaped pressure sensitive electrically conductive material of which electrical resistance value varies depending on pressure in the vertical direction in such a manner that the electrode surfaces alternately appears on the upper surface and the rear surface of the sheet-shaped pressure sensitive electrically conductive material, and the wire-shaped electrode material are arranged in the lateral direction at right angles to the vertical direction, and intersections defined by the electrode members arranged in the vertical direction and the horizontal direction sandwich or clamp the sheet-shaped pressure sensitive electrically conductive material from both the surfaces. Accordingly, by measuring the electrical resistance value at the intersection defined by the electrode members arranged in the vertical direction and the lateral direction, the load at the foregoing intersection, i.e., the pressure can be detected. In such a manner, by arranging the electrode members on the sheet-shaped pressure sensitive electrically conductive material, the conventional multi-layered structure is changed to a single layered composite structure, whereby flexibility and durability to repeated bending can be improved without any usage of a sheet-shaped material for constructing the electrodes such as a flexible base plate or the like.

Other and further objects, features and advantages of the present invention will become more apparent from the following description of preferred embodiments with reference to the accompanying drawings.

BRIEF DESCRIPTION OF THE DRAWINGS

The present invention will be understood more fully from the detailed description given hereinafter and from the accompanying drawings of the preferred embodiment of the invention, which, however, should not be taken to be limitative to the present invention, but are for explanation and understanding only.

In the drawings.

DESCRIPTION OF A PREFERRED

The present invention will be described in detail hereinafter with reference to the accompanying drawings which illustrate a preferred embodiment thereof.

Figure 5:
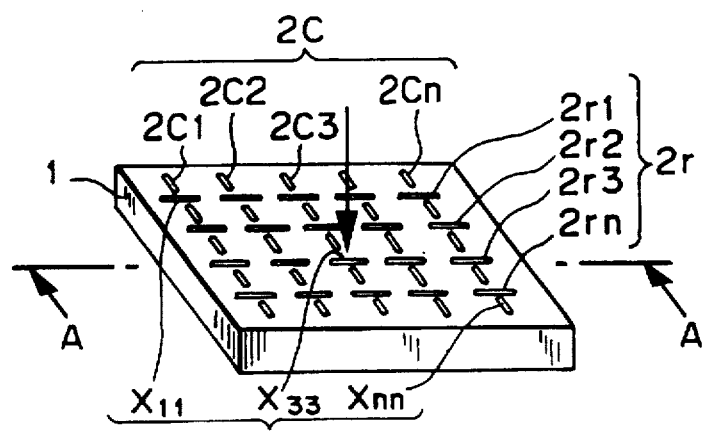
FIG. 5 is a perspective view showing a distributed pressure sensor constructed according to an embodiment of the present invention.
Figure 6:
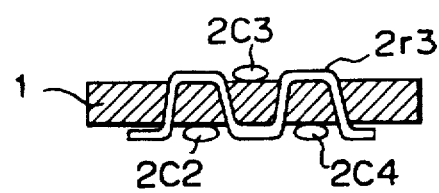
FIG. 6 is a cross sectional view showing the distributed pressure sensor taken along line A—A in FIG. 5.

FIG. 5 and FIG. 6 show a distributed pressure sensor according to an embodiment of the present invention. FIG. 5 is a schematic perspective view of the distributed pressure sensor of the present invention, and FIG. 6 is a schematic cross sectional view of the distributed pressure sensor taken along the line A—A in FIG. 5.

In FIG. 5, reference numeral 1 denotes a sheet-shaped substrate formed of a pressure sensitive electrically conductive material, and reference numerals 2c and 2r denote each an electrode member. As the electrode member 2c and 2r, there can be used a wire having a high flexibility comprising braided fine wires or a wire having a high flexibility comprising a copper wire plated with gold or silver.

As shown in FIG. 6, the wire-shaped electrode members include a plurality of horizontal or transverse electrode rows 2r (2r1, 2r2, 2r3, ..., 2rn) and vertical electrode columns 2c (2c1, 2c2, 2c3, 2cn). The horizontal electrodes 2r were arranged so that they are put through the pressure sensitive electrically conductive substrate 1 of, e.g., 0.5 mm thick with reciprocating and alternately emerging on the upper surface and on the rear surface of the pressure sensitive conductive substrate 1. The vertical electrodes 2c were arranged in the same manner as the horizontal electrodes 2r except that the electrodes 2c are at right angles to the electrodes 2r when viewed in an imaginary projected plan view. The electrode members 2r and 2c (2r1, 2r2, 2r3, ..., 2rn, 2c1, 2c2, 2c3, ..., 2cn) are arranged equidistantly, e.g., at a distance of 5 mm from each other in both the directions. A matrix formed by the electrode rows 2r and the electrode columns 2c defines a plurality of intersections X (e.g., (2r3, 2c3), etc.). The two electrode members 2r and 2c sandwich or clamp therebetween the pressure sensitive conductive substrate 1 at every intersection. In spatial relationship, the electrode members 2r and 2c do not contact each other but may only come closer to each other when pressure is exerted on the substrate.

Figure 7:
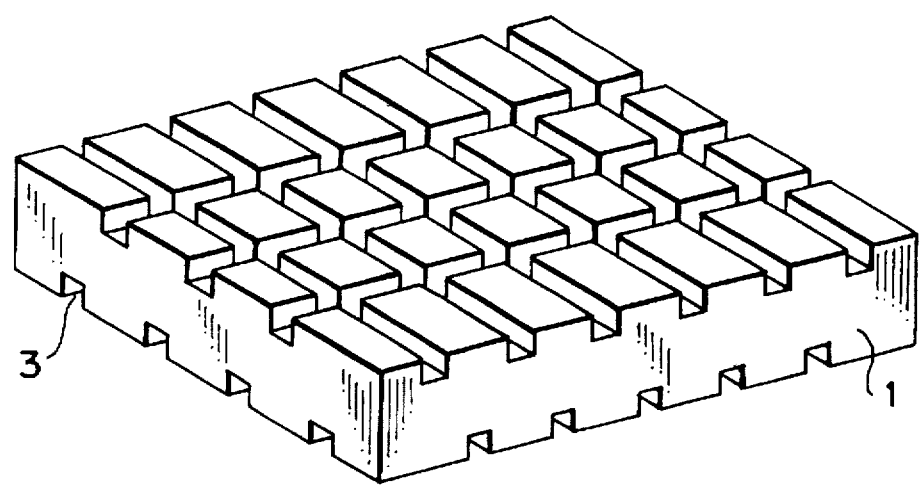
FIG. 7 is a perspective view showing a substrate with a plurality of cuts or grooves for use in a distributed pressure sensor.
Figure 8:
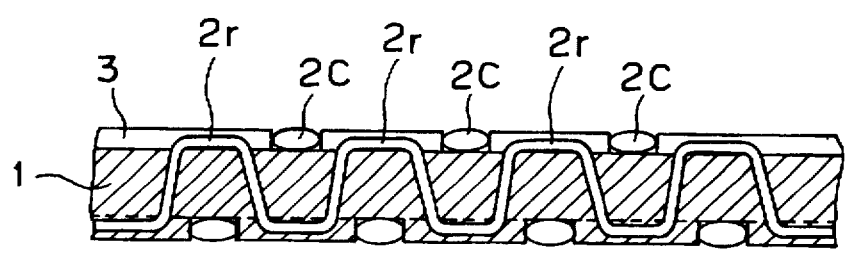
FIG. 8 is a cross-sectional view showing a substrate with a plurality of cuts or grooves in which threads are embedded.

The above-described pressure sensor of the present invention can be fabricated, for example, by sewing the sheet-shaped pressure sensitive electrically conductive substrate 1 with a thread of the electrode member so that the electrode member appear on the upper and lower surfaces of the substrate 1 alternately as shown in FIGS. 5 and 6. To facilitate the sewing, the conductive substrate 1 may be formed, with a cutter or the like means of cutting, of a plurality of narrow, shallow cuts or grooves 3 in which the substrate is thinner than outside the cuts 3, as shown in FIGS. 7 and 8, so that not only a thread of the electrode member 2c or 2r is sewn with ease but also the thread is embedded in the cuts 3. Thus, provision of the cuts or grooves 3 allows down-sizing of the sensor and also makes the resulting sensor more suitable for use since it can have a more even or flat surface. It is of course possible to sew the pressure sensitive electrically conductive substrate 1 with the thread of the electrode material without preliminary forming the cuts on the pressure sensitive electrically conductive substrate 1 since the pressure sensitive electric electrically conductive material is a soft material.

In such a manner, a plurality of pressure detecting points are formed at the intersections defined by the electrode rows 2r and the electrode columns 2c.

With the above-described construction, while the foregoing state is maintained, application of a certain load to, e.g., an intersection X (2r3, 2c3), decreases the volume of the sheet-shaped pressure sensitive electrically conductive substrate 1 at the intersection X, which in turn reduces an electrical resistance value at the part of the intersection X. A load on the intersection X can be obtained from the variation of the resistance value. That is, first selection is made of the electrode row, e.g., 2r3 and the electrode column, e.g., 2c3, i.e., intersecting point X=X33 (2r3, 2c3), and then measurement is made of a resistance of the portion of the conductive substrate 1 at the point X33 (the portion of the conductive substrate 1 sandwiched by the electrode members 2r3 and 2c3). The data thus obtained is used as a basis for the calculation of a load applied to the part X33, which calculation can be made in a conventional manner. By sequentially measuring resistances of the portion of the conductive substrate at various intersections X and obtaining data on loads exerted on the portions at various intersections X, information on the distribution of pressure on the surface of, e.g., a human body can be obtained in a conventional manner. This sequential measurement can be performed by using a scanning portion a first control circuit (not shown) which applies a voltage to the plurality of conductors 2r (or 2c) on the substrate 1 in a predetermined scanning order and a second control circuit (not shown) which sequentially receives signals from the plurality of the conductors 2c (or 2r) on the substrate 1 in a predetermined order. The information on the distribution of pressure can be visualized on a CRT by a conventional manner by inputting signals for determining the order of scanning by the first control circuit and signals for determining the order of scanning by the second control circuit to a CRT as X (horizontal) and Y (vertical) signals, respectively, and also inputting to the CRT output signals from the second control circuit as a Z (brightness) signal so that the distribution of pressure can be displayed in brightness (e.g., Japanese Patent Application Laying-open No. 42021/1980).

Figure 1:
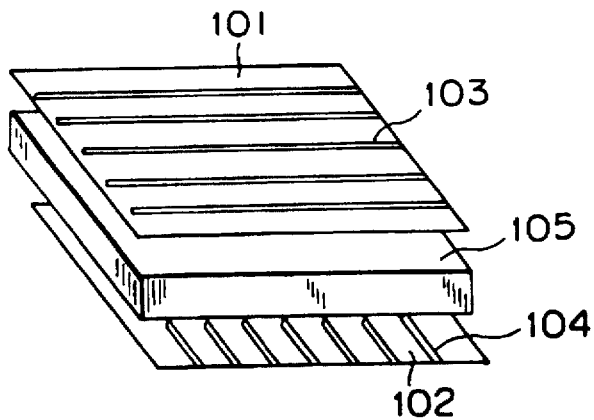
FIG. 1 is a schematic exploded perspective view showing a conventional distributed pressure sensor.
Figure 2:
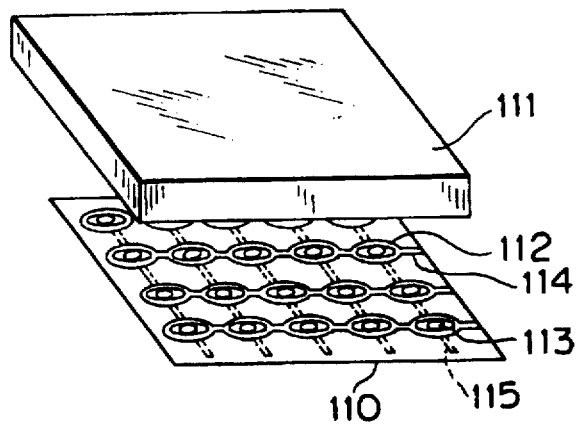
FIG. 2 is a schematic exploded perspective view showing another conventional distributed pressure sensor.
Figure 3:
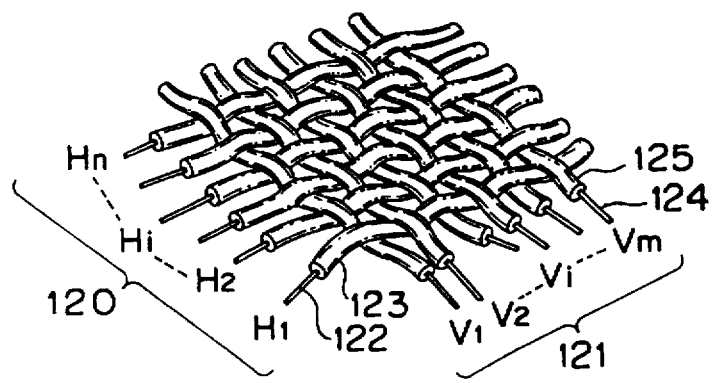
FIG. 3 is a perspective view showing a conventional distributed pressure sensor.
Figure 4:
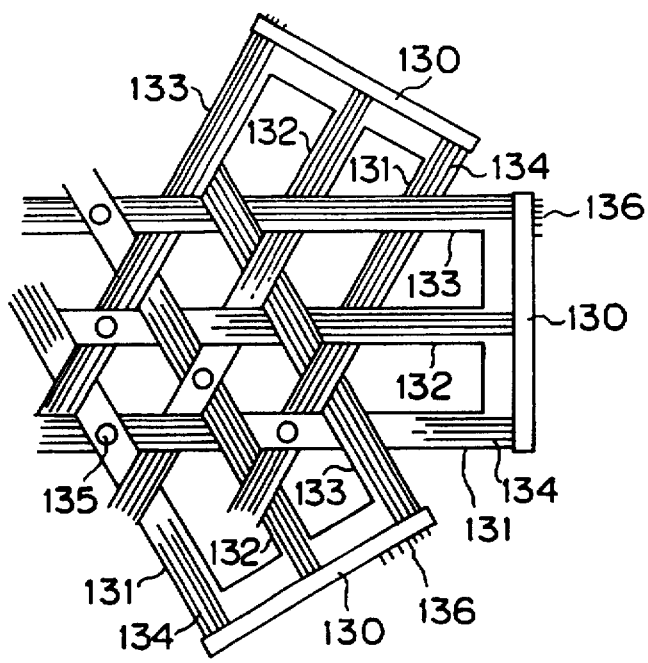
FIG. 4 is a plan view showing another conventional distributed pressure sensor.

Sometimes, it may be not easy to obtain an exact value of the resistance value variation due to the occurrence of an electric current turn-around phenomenon. However, the deviation or fluctuation of the data due to this phenomenon may be corrected in a conventional manner, e.g., by employing the technology as disclosed in Japanese Patent Application Laying-open No. 42021/1980 or Japanese Patent Application Laying-open No. 102127/1987. For example, each of the pressure detecting sensors may be connected to an FET (field effect transistor) which operates in response to an address signal from a control circuit, which scans the sensors sequentially, to form a switching circuit, and information on the distribution of pressure from each pressure detecting sensors through the switching circuit is outputted in the form of video signals (cf. FIG. 2 of Japanese Patent Application Laying-open No. 102127/1987).

As is apparent from the above description, according to the present invention, increasing of the flexibility, constructing of the sensor having a reduced thickness, increasing of the durability to repeated bending or a similar effect can be obtained. The sensor of the present invention can exhibit a power when especially the sensor is attached to a human body to detect a contact pressure with an article to be tested.

While the present invention has been described above only with a single preferred embodiment, it should of course be understood that the present invention should not be limited only to this embodiment but various change or modification may be made without departure from the scope of the present invention as defined by the appended claims.

What is claimed is:

1. A distributed pressure sensor comprising:
   a sheet-shaped substrate comprising an electrically conductive material whose electric resistance varies in response to pressure exerted thereon;
   a first electrode member provided on said substrate, said first electrode member being linear and appearing reciprocating and alternately on opposite surfaces of said substrate at a predetermined interval;
   a second electrode member provided on said substrate, said second electrode member being linear and appearing reciprocating and alternately on said opposite surfaces of said substrate at a predetermined interval at right angles to said first electrode member;
   said first and second electrode members intersecting each other in an imaginary projected plan view;
   wherein a portion of said first electrode member and a portion of said second electrode member sandwiching said substrate at each intersection in said imaginary projected plan view between said first and second electrode members to define intersection portions.

2. The distributed pressure sensor as claimed in claim 1, wherein said first and second linear electrode members are sewn to said substrate.

3. The distributed pressure sensor as claimed in claim 1, wherein said first and second linear electrode members each comprises a plurality of electrodes arranged equidistantly in the form of a matrix.

4. The distributed pressure sensor as claimed in claim 1, wherein said substrate is provided with a plurality of cuts in said opposite surfaces.

5. The distributed pressure sensor as claimed in claim 4, wherein at least one of said first and second electrode members are arranged in said cut.

6. The distributed pressure sensor as claimed in claim 5, wherein said at least one of the first and second electrode members is embedded in said cut.

7. The distributed pressure sensor as claimed in claim 1, wherein said pressure sensitive conductive material comprises carbon particles.

8. The distributed pressure sensor as claimed in claim 1, wherein at least one of said first and second electrode members comprises braided fine wires.

9. The distributed pressure sensor as claimed in claim 1, wherein at least one of said first and second linear electrode members comprises a copper wire plated with a metal selected from the group consisting of gold and silver.

10. The distributed pressure sensor as claimed in claim 2, wherein said first and second linear electrode members each comprises a plurality of electrodes arranged equidistantly in the form of a matrix.

11. The distributed pressure sensor as claimed in claim 2, wherein said substrate is provided with a plurality of cuts in said opposite surfaces.

12. The distributed pressure sensor as claimed in claim 11, wherein at least one of said first and second electrode members are arranged in said cut.

13. The distributed pressure sensor as claimed in claim 12, wherein said at least one of the first and second electrode members is embedded in said cut.

14. The distributed pressure sensor as claimed in claim 2, wherein said pressure sensitive conductive material comprises carbon particles.

15. The distributed pressure sensor as claimed in claim 2, wherein at least one of said first and second electrode members comprises braided fine wires.

16. The distributed pressure sensor as claimed in claim 2, wherein at least one of said first and second linear electrode members comprises a copper wire plated with a metal selected from the group consisting of gold and silver.

17. A method for manufacturing a distributed pressure sensor, comprising the steps of:
   providing a sheet-shaped substrate comprising an electrically conductive material whose electric resistance varies in response to pressure exerted thereon;
   sewing said substrate with a first linear conductor so that said conductor partly appearing reciprocating and alternately on opposite surfaces of said substrate at a predetermined interval; and
   sewing said substrate with a second linear conductor so that said conductor partly appearing reciprocating and alternately on said opposite surfaces of said substrate at a predetermined interval at right angles to said first electrode member.

* * * * *